United States Patent [19]

Mark et al.

[11] Patent Number: 4,520,187

[45] Date of Patent: May 28, 1985

[54] POLYCARBONATES AND POLYESTER CARBONATES EXHIBITING IMPROVED HEAT RESISTANCE

[75] Inventors: Victor Mark, Evansville; Charles V. Hedges, Mt. Vernon, both of Ind.

[73] Assignee: General Electric Company, Mt. Vernon, Ind.

[21] Appl. No.: 451,109

[22] Filed: Dec. 17, 1982

[51] Int. Cl.³ .................... C08G 63/62; C08G 63/64
[52] U.S. Cl. ............................. 528/176; 528/125; 528/126; 528/128; 528/173; 528/174; 528/193; 528/194; 528/196; 528/198; 528/199; 528/200; 528/201; 528/202; 528/204; 568/722; 568/723; 568/726
[58] Field of Search ............... 528/125, 126, 128, 174, 528/176, 173, 196, 198, 199, 200, 201, 202, 204, 193, 194; 568/722, 723, 726

[56] References Cited

U.S. PATENT DOCUMENTS

| | | | |
|---|---|---|---|
| 3,028,364 | 4/1962 | Conix et al. | 528/196 |
| 3,136,741 | 6/1964 | Schnell et al. | 528/196 |
| 3,255,230 | 6/1966 | Kurkjy et al. | 528/196 |
| 3,312,660 | 4/1967 | Kurkjy et al. | 528/196 |
| 3,312,661 | 4/1967 | Kurkjy et al. | 528/196 |
| 4,304,899 | 12/1981 | Mark et al. | 528/196 |

Primary Examiner—Lester L. Lee
Attorney, Agent, or Firm—Myron B. Kapustij; Martin B. Barancik

[57] ABSTRACT

Novel heat resistant polycarbonates are provided which are the polymerized reaction products of:
(i) a carbonate precursor; and
(ii) at least one dihydric phenol selected from dihydric phenols represented by the general formulae

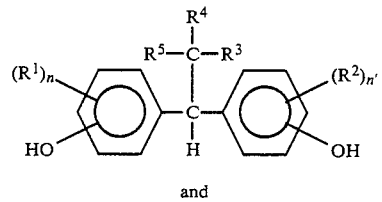

and

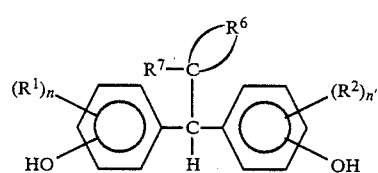

wherein:
each $R^1$ is independently selected from halogen radicals, monovalent hydrocarbon radicals, and monovalent hydrocarbonoxy radicals;
each $R^2$ is independently selected from halogen radicals, monovalent hydrocarbon radicals, and monovalent hydrocarbonoxy radicals;
$R^4$ and $R^5$ are independently selected from monovalent hydrocarbon radicals;
$R^3$ is selected from hydrogen and monovalent hydrocarbon radicals, with the proviso that if $R^3$ is a hydrogen radical than at least one of the monovalent hydrocarbon radicals represented by $R^4$ and $R^5$ contains at least two carbon atoms;
$R^7$ is selected from hydrogen and monovalent hydrocarbon radicals;
$R^6$ is a divalent hydrocarbon radicals; and n and n' are independently selected from whole numbers having a value of from 0 to 4 inclusive.

40 Claims, No Drawings

POLYCARBONATES AND POLYESTER CARBONATES EXHIBITING IMPROVED HEAT RESISTANCE

BACKGROUND OF THE INVENTION

Polycarbonates are well known thermoplastic materials which due to their many excellent properties find use as thermoplastic engineering materials in many commercial and industrial applications. The polycarbonates exhibit, for example, excellent properties of toughness, flexibility, impact strength, and the like. The polycarbonates are generally prepared by the reaction of a dihydric phenol, such as bisphenol-A, with a carbonate precursor, such as phosgene.

While the conventional polycarbonates are in general quite suitable for a wide variety of uses, there nevertheless exists a need, especially in high temperature environments, for polycarbonates exhibiting, to a substantial degree, most of the other advantageous properties of conventional polycarbonates, and simultaneously exhibiting higher heat resistance than that possessed by conventional polycarbonates.

It is, therefore, an object of the instant invention to provide polycarbonates which exhibit, to a substantial degree, substantially most of the advantageous properties of conventional polycarbonates while simultaneously exhibiting improved heat resistance.

SUMMARY OF THE INVENTION

In accordance with the instant invention there are provided novel polycarbonates exhibiting, to a substantial degree, substantially most or all of the advantageous properties of conventional polycarbonates and simultaneously exhibiting improved heat resistance. The novel polycarbonates of the instant invention are prepared by reacting a carbonate precursor with a dihydric phenol selected from dihydric phenols represented by the general formulae

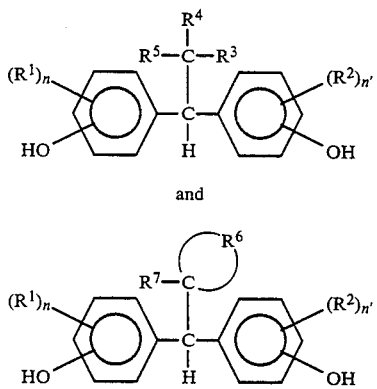

wherein:

$R^4$ and $R^5$ are independently selected from monovalent hydrocarbon radicals;

$R^3$ is selected from monovalent hydrocarbon radicals and hydrogen radical, with the proviso that if $R^3$ is a hydrogen radical than at least one of the monovalent hydrocarbon radicals represented by $R^4$ and $R^5$ must contain at least two carbon atoms;

$R^6$ is a divalent hydrocarbon radical which together with the carbon atoms C forms a cyclic hydrocarbon structure;

$R^7$ is selected from hydrogen and monovalent hydrocarbon radicals;

$R^1$ is independently selected from halogen radicals, monovalent hydrocarbon radicals, and monovalent hydrocarbonoxy radicals, $R^2$ is independently selected from halogen radicals, monovalent hydrocarbon radicals, and monovalent hydrocarbonoxy radicals; and n and n' are independently selected from whole numbers having a value of from 0 to 4 inclusive.

DESCRIPTION OF THE INVENTION

In accordance with the instant invention there are provided novel polycarbonates which exhibit, to a substantial degree, most of the advantageous properties of conventional polycarbonates and also exhibit good thermal characteristics such as good heat resistance.

The novel polycarbonates of the instant invention are derived from (i) a carbonate precursor, and (ii) at least one dihydric phenol selected from dihydric phenols represented by the general formulae

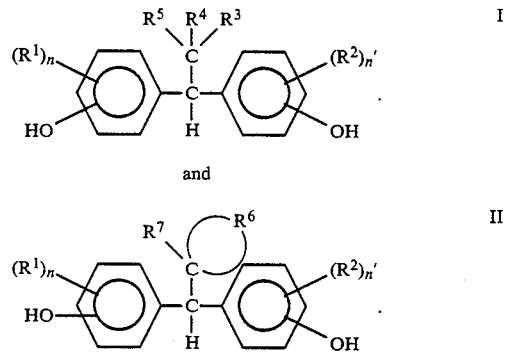

In Formula I $R^4$ and $R^5$ are independently selected from monovalent hydrocarbon radicals; $R^3$ is selected from hydrogen and monovalent hydrocarbon radicals, with the proviso that if $R^3$ is hydrogen than at least one of the monovalent hydrocarbon radicals represented by $R^4$ and $R^5$ contains at least two carbon atoms; $R^1$ is independently selected from halogen radicals, monovalent hydrocarbon radicals, and monovalent hydrocarbonoxy radicals; $R^2$ is independently selected from halogen radicals, monovalent hydrocarbon radicals, and monovalent hydrocarbonoxy radicals; and n and n' are independently selected from whole numbers having a value of from 0 to 4 inclusive.

In Formula II $R^1$, $R^2$, n and n' are as defined hereinabove; $R^7$ is selected from hydrogen and monovalent hydrocarbon radicals; and $R^6$ is a divalent hydrocarbon radical which together with the C radical to which it is bonded forms a cyclic hydrocarbon structure.

The preferred halogen radicals represented by $R^1$ and $R^2$ are chlorine and bromine.

The monovalent hydrocarbon radicals represented by $R^1$ and $R^2$ are selected from alkyl radicals, aryl radicals, alkaryl radicals, aralkyl radicals, and cycloalkyl radicals. The preferred alkyl radicals represented by $R^1$ and $R^2$ are those containing from 1 to about 6 carbon atoms. These preferred alkyl radicals include the straight chain and the branched alkyl radicals. Some non-limiting illustrative examples of these preferred alkyl radicals include methyl, ethyl, propyl, isopropyl, butyl, isobutyl, tertiarybutyl, and the like. The preferred aryl radicals represented by $R^1$ and $R^2$ are those containing from 6 to 12 carbon atoms and include phenyl, naphthyl, and biphenyl. The preferred alkaryl and aralkyl radicals represented by $R^1$ and $R^2$ are those containing from 7 to about 14 carbon atoms and include benzyl, tolyl, ethylphenyl, and the like. The preferred cycloalkyl radicals represented by $R^1$ and $R^2$ are those containing from 3 to about 8 ring carbon atoms and include cyclopropyl, cyclopentyl, cyclohexyl, and the like.

The monovalent hydrocarbonoxy radicals represented by $R^1$ and $R^2$ are preferably selected from alkoxy radicals and aryloxy radicals. The preferred alkoxy radicals are those containing from 1 to about 6 carbon atoms. The preferred aryloxy radical is the phenoxy radical.

In the dihydric phenols of Formulae I and II when more than one $R^1$ substituent is present, i.e., when n is equal to from 2–4, they may be the same or different. The same is true for the $R^2$ substituent. If n or n' is zero than the ring carbon atoms of the aromtic nuclear residue are substituted with hydrogen atoms.

The monovalent hydrocarbon radicals represented by $R^3$, $R^4$, $R^5$, and $R^7$ are selected from alkyl radicals, cycloalkyl radicals, aryl radicals, alkaryl radicals, and aralkyl radicals.

The preferred alkyl radicals represented by $R^3$, $R^4$, $R^5$, and $R^7$ are those containing from 1 to about 8 carbon atoms. These alkyl radicals include the branched alkyl radicals and the straight chain alkyl radicals. Some illustrative non-limiting examples of these preferred alkyl radicals include methyl, ethyl, propyl, butyl, isobutyl, tertiarybutyl, pentyl, neopentyl, and the like.

The preferred aryl radicals represented by $R^3$, $R^4$, $R^5$, and $R^7$ are those containing from 6 to 12 carbon atoms, i.e., phenyl, naphthyl and biphenyl. The preferred alkaryl and aralkyl radicals are those containing from 7 to about 14 carbon atoms, e.g., benzyl, tolyl, ethylphenyl, etc.

The preferred cycloalkyl radicals represented by $R^3$, $R^4$, $R^5$ and $R^7$ are those containing from 4 to about 8 ring carbon atoms. Some illustrative non-limiting examples of these preferred cycloalkyl radicals inclyde cyclobutyl, cyclopentyl, cyclohexyl, and the like.

As mentioned previously $R^6$ is a divalent radical which together with the

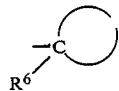

radical forms a cyclic hydrocarbon structure. This cyclic structure may be monocyclic or bicyclic. Preferably $R^6$ is a divalent alkylene radical containing from 3 to about 8 carbon atoms, e.g., propylene, butylene, pentylene, and the like.

Some illustrative non-limiting examples of the cyclic structures formed by $R^6$ and the carbon radical described above include:

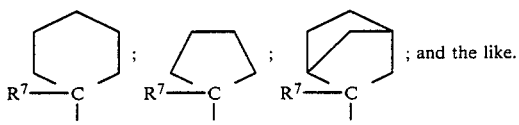
; and the like.

Particularly useful, and sometimes even preferred, dihydric phenols of Formula I are those wherein all of $R^3$, $R^4$, and $R^5$ are independently selected from monovalent hydrocarbon radicals.

The novel dihydric phenols of Formulae I and II are prepared by the reaction of a particular aldehyde with a phenol in the presence of an acid catalyst. The particular aldehyde reactant is selected from aldehydes represented by the general formulae

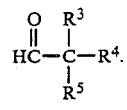 III and

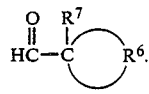 IV wherein $R^3$, $R^4$, $R^5$, $R^6$ and $R^7$ are as defined hereinafore. The phenol reactants are selected from phenols represented by the general formulae

 V and

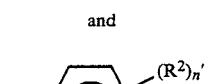 VI wherein $R^1$, $R^2$, n and n' are as defined hereinafore.

In order to obtain the novel dihydric phenols of Formula I one mole of an aldehyde of Formula III is reacted with one mole of a phenol of Formula V and one mole of a phenol of Formula VI in the presence of an acid catalyst. Some illustrative non-limiting examples of suitable acid catalysts that may be employed include hydrochloric acid, hydrobromic acid, poly(styrene sulfonic acid), sulfuric acid, benzene sulfonic acid, and the like. The phenols of Formulae V and VI are reacted with the aldehyde of Formula III under conditions of temperature and pressure, and in the presence of said acid catalyst, such that coreaction between said phenols and said aldehyde will occur to form the dihydric phenol of Formula I. The reaction, generally, proceeds satisfactorily at about one atmosphere of pressure and at temperatures of from room temperature to about 100° C.

The amount of the acid catalyst employed is a catalytic amount. By catalytic amount is meant an amount effective to catalyze the reaction between the aldehyde and the phenol. Generally this amount is in the range of from about 0.1 to about 10%. However, in actual practice it is usually somewhat higher since the water coproduct formed in the reaction dilutes the acid catalyst and makes it somewhat less effective (slowing the reaction) than in its undiluted state.

The phenols of Formula V and VI may, of course, be the same. In that case one mole of the aldehyde of Formula III is reacted with two moles of the phenol.

In order to obtain the dihydric phenols of Formula II one mole of an aldehyde of Formula IV is reacted with one mole of the phenol of Formula V and one mole of the phenol of Formula VI, or if the phenols of Formulae V and VI are the same with two moles of the phenol, under the reaction conditions and in the presence of an acid catalyst as set forth above to produce the dihydric phenol of Formula II.

Some nonlimiting illustrative examples of the dihydric phenols represented by Formula I include:

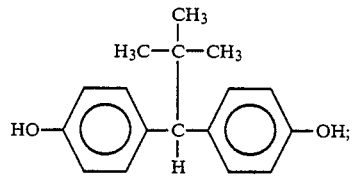

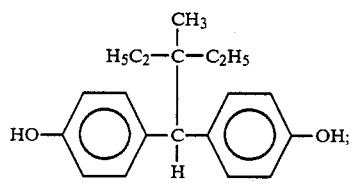

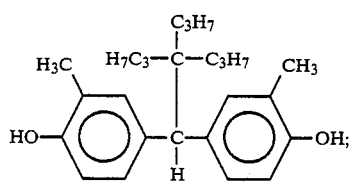

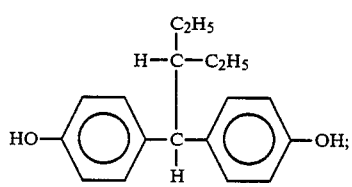

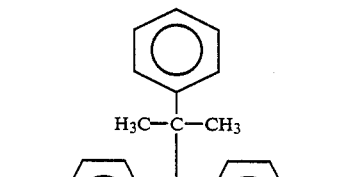

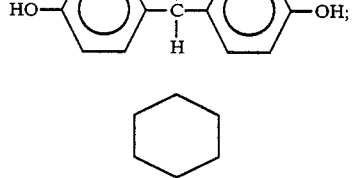

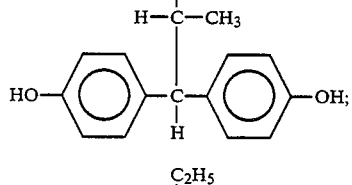

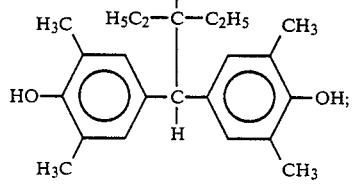

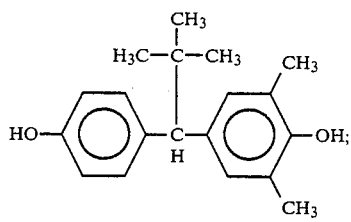

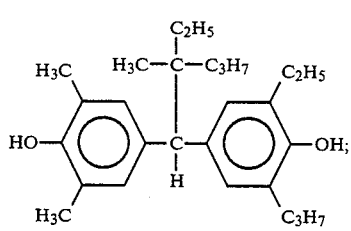

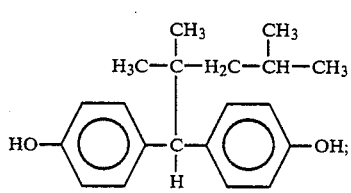

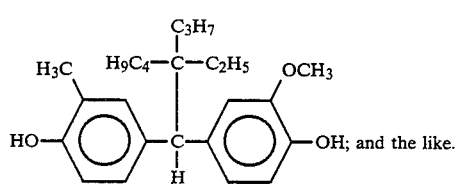

and the like.

Some illustrative non-limiting examples of the dihydric phenols represented by Formula II include:

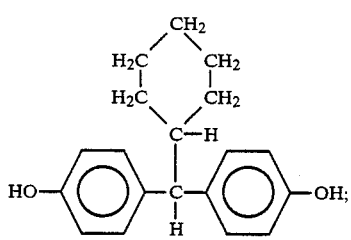

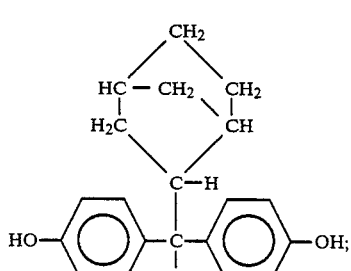

-continued

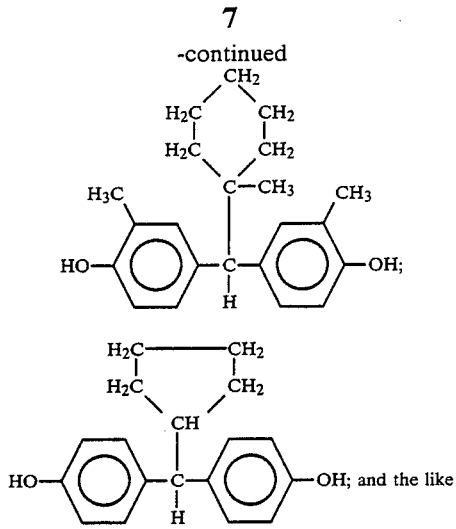

In the preparation of the carbonate polymers of the instant invention only one dihydric phenol of Formulae I or II may be used, or a mixture of two or more different dihydric phenols of Formulae I and/or II may be employed. Thus, for example, two or more different dihydric phenols of Formula I may be used; two or more different dihydric phenols of Formula II may be used; or at least one dihydric phenol of Formula I and at least one dihydric phenol of Formula II may be used.

The carbonate precursor may be a carbonyl halide, a diarylcarbonate, or a bishaloformate. The preferred carbonate precursors are the carbonyl halides. The preferred carbonyl halides include carbonyl chloride, carbonyl bromide, and mixtures thereof. The preferred carbonyl halide is carbonyl chloride, also known as phosgene.

The novel carbonate polymers of the instant invention contain repeating structural units represented by the general formulae

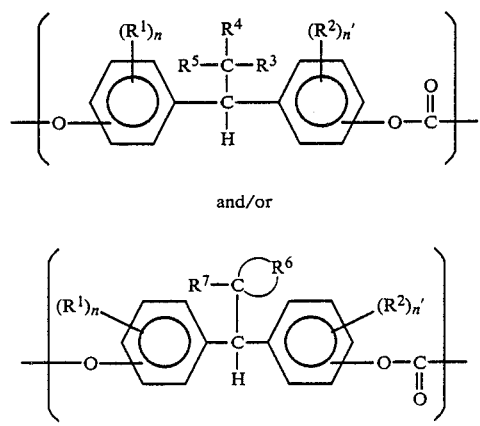

wherein $R^1$, $R^2$, $R^3$, $R^4$, $R^5$, $R^6$, $R^7$, n and n' are as defined above.

These high molecular weight aromatic carbonate polymers generally have a weight average molecular weight in the range of from about 10,000 to about 150,000, preferably from about 20,000 to about 100,000.

One method of preparing the high molecular weight aromatic carbonate polymers of the instant invention involves the heterogeneous interfacial polymerization system utilizing an aqueous caustic solution, an organic water immiscible solvent such as methylene chloride, at least one dihydric phenol selected from phenols represented by Formulae I and II, a carbonate precursor such as phosgene, a catalyst, and a molecular weight regulator.

Another useful method for preparing the carbonate polymers of the instant invention involves the use of an organic solvent system wherein the organic solvent system may also function as an acid acceptor, at least one dihydric phenol of Formula I and/or II, a molecular weight regulator, a catalyst, a carbonate precursor such as phosgene, and a molecular weight regulator.

The catalysts which are employed herein can be any of the suitable catalysts that aid the polymerization of a dihydric phenol with phosgene. Suitable catalysts include, but are not limited to, tertiary amines such as triethylamine, quaternary ammonium compounds, and quaternary phosphonium compounds.

The molecular weight regulators employed may be any of the known compounds which regulate the molecular weight of the carbonate polymer by a chain terminating mechanism. These compounds include, but are not limited to phenol, tertiary butyl phenol, and the like.

The temperature at which phosgenation reaction proceeds may vary from below 0° C. to above 100° C. The reaction proceeds satisfactorily at temperatures from room temperature, about 25° C. to 50° C. Since the reaction is exothermic, the rate of phosgene addition or a low boiling solvent such as methylene chloride may be used to control the reaction temperature.

The carbonate polymers of the instant invention may optionally have admixed therewith certain commonly known and used additives such as antioxidants; antistatic agents; fillers such as glass fibers, mica, talc, clay, and the like; impact modifiers; ultraviolet radiation absorbers such as the benzophenones and the benzotriazoles; plasticizers; hydrolytic stabilizers such as the epoxides disclosed in U.S. Pat. Nos. 3,489,716; 4,138,379 and 3,839,247, all of which are incorporated herein by reference; color stabilizers such as the organophosphites disclosed in U.S. Pat. Nos. 3,305,520 and 4,118,370, both of which are incorporated herein by reference and flame retardants.

Some particularly useful flame retardants are the alkali and alkaline earth metal salts of sulfonic acids. These types of flame retardants are disclosed in U.S. Pat. Nos. 3,933,734; 3,948,851; 3,926,908; 3,919,167; 3,909,490; 3,953,396; 3,931,100; 3,978,024; 3,953,399; 3,917,559; 3,951,910 and 3,940,366, all of which are incorporated herein by reference.

Another embodiment of the instant invention is a carbonate copolymer obtained by reacting, as essential components, (i) a carbonate precursor, (ii) at least one dihydric phenol selected from the dihydric phenols represented by Formulae I and II, and (iii) at least one dihydric phenol represented by the general formula

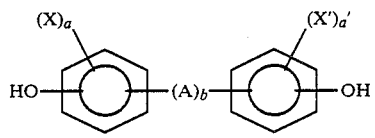

wherein A represents an alkylene radical, a cycloalkylene radical; an alkylidene radical, a cycloalkylidene radical,

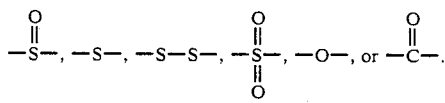

The dihydric phenols of Formula IX are well known and are generally used in making conventional polycarbonates.

In Formula IX each X' and X are independently selected from halogen radicals, such as chlorine and bromine; monovalent hydrocarbon radicals; and monovalent hydrocarbonoxy radicals. The monovalent hydrocarbon radicals are selected from alkyl radicals, preferably those containing from 1 to about 6 carbon atoms; aryl radicals, preferably those containing from 6 to 12 carbon atoms such as phenyl, naphthyl, and biphenyl; alkaryl radicals and aralkyl radicals, preferably those containing from 7 to about 14 carbon atoms; and cycloalkyl radicals, preferably those containing from 4 to about 8 ring carbon atoms.

The monovalent hydrocarbonoxy radicals represented by X and X' are preferably selected from alkoxy radicals and aryloxy radicals. The letters a and a' independently represent whole numbers having a value of from 0 to 4, inclusive. The letter b is either zero or one.

The alkylene radicals represented by A are those containing from 2 to about 6 carbon atoms. The alkylidene radicals represented by A are those containing from 1 to about 6 carbon atoms. The cycloalkylene and cycloalkylidene radicals represented by A are those containing from 4 to about 7 ring carbon atoms. The alkylene and alkylidene radicals represented by A are straight chain alkylene and alkylidene radicals.

In the dihydric phenol compounds represented by Formula IX when more than one X substituent is present they may be the same or different. The same is true for the X' substituents. Where b is zero in Formula IX the aromatic rings are directly joined with no intervening alkylene or other bridge. The positions of the hydroxyl groups and X or X' on the aromatic nuclear residues can be varied in the ortho, meta, or para positions and the groupings can be in a vicinal, asymmetrical or symmetrical relationship, where two or more ring carbon atoms of the aromatic hydrocarbon residue are substituted with X or X' and hydroxyl groups.

Some non-limiting illustrative examples of suitable dihydric phenols represented by Formula IX include:
1,1-bis(4-hydroxyphenyl)cyclohexane;
2,2-bis(4-hydroxyphenyl)propane (bisphenol-A);
3,3-bis(3-methyl-4-hydroxyphenyl)pentane;
1,1-bis(3-methyl-4-hydroxyphenyl)ethane;
2,2-bis(3,5-dibromo-4-hydroxyphenyl)propane;
3,3'-dichloro-4,4'-dihydroxydiphenyl;
bis(3-chloro-4-hydroxphenyl)sulfone;
3,3'-diethyl-4,4'-dihydroxydiphenyl;
bis(4-hydroxphenyl)sulfide; and the like.

The amount of the dihydric phenols of Formulae I and/or II utilized in this embodiment is an amount effective to improve the heat resistance, e.g., glass transition temperature, of the copolymers. This amount is generally in the range of from about 10 to about 90 weight percent, preferably from 30-70 weight percent, based on the toatal amount of dihydric phenol used, i.e., the total amount of the dihydric phenols of Formulae I and/or II, and IX present. The preferred dihydric phenol of Formula IX is 2,2-bis(4-hydroxyphenyl)propane.

The carbonate copolymers obtained by reacting (i) a carbonate precursor, (ii) at least one dihydric phenol selected from dihydric phenols represented by Formulae I and II, and (iii) at least one dihydric phenol represented by Formula IX will contain the following repeating structural units:

VII; and/or VIII; and

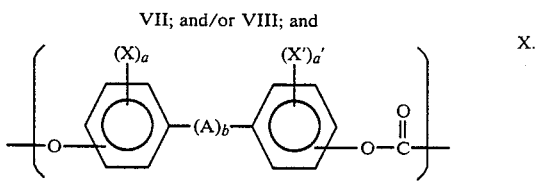

X.

wherein X, X', a, a', A and b are as defined hereinafore.

When only the dihydric phenols of Formula I and Formula IX are utilized the resultant carbonate polymer will contain repeating structural units VII and X. When only dihydric phenols of Formulae II and IX are used the resultant polycarbonate will contain only repeating structural units VIII and X. When dihydric phenols of Formulae I, II and IX are used the resultant polycarbonate will contain repeating structural units of Formulae VII, VIII and X.

The relative amounts of the various repeating structural units present in the copolymer will generally depend on the amount of the various dihydric phenols utilized in preparing the copolymer.

The procedures for producing the carbonate copolymers are generally similar to those described hereinafore for producing the polymers of the instant invention. The carbonate copolymers may likewise have admixed therewith the various additives described supra.

Yet another embodiment of the instant invention is a polycarbonate resin blend comprised of (i) at least one polycarbonate resin of the instant invention (hereinafter referred to as resin A); and (ii) at least one polycarbonate resin derived from (a) a carbonate precursor, and (b) at least one dihydric phenol of Formula IX (hereinafter referred to as resin B). These blends may generally contain from about 10 to about 90 weight percent of resin A, based on the total amount of resins A and B present in the blends. The instant blends are prepared by first preforming the various resins and thereafter physically mixing or blending these resins together. These blends may optionally contain the various additives described supra.

Still another embodiment of the instant invention are copolyester-carbonates derived from (i) a carbonate precursor; (ii) at least one dihydric phenol selected from dihydric phenols represented by general Formulae I and II; and (iii) at least one difunctional carboxylic acid or a reactive derivative thereof.

Briefly stated, the copolyester-carbonates comprise recurring carbonate groups

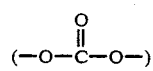

carboxylate groups

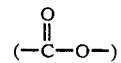

and aromatic carbocyclic groups in the linear polymer chain, in which at least some of the carboxylate groups and at least some of the carbonate groups are bonded directly to ring carbon atoms of the aromatic carbocyclic groups.

These copolyester-carbonate polymers contain ester and carbonate linkages in the polymer chain, wherein the amount of ester linkages is in the range of from about 25 to about 90 mole percent, preferably in the range of from about 35 to about 80 mole percent.

Copolyester-carbonates in general, and methods for their preparation are disclosed in U.S. Pat. No. 3,169,121, which is hereby incorporated herein by reference.

In general, any difunctional carboxylic acid conventionally used in the preparation of linear polyesters may be utilized in the preparation of the copolyester-carbonates of the present invention. The carboxylic acids which may be used include the aliphatic carboxylic acids, aliphatic-aromatic carboxylic acids, and aromatic carboxylic acids. These acids are disclosed in the aforementioned U.S. Pat. No. 3,169,121.

The carboxylic acids which may be utilized in the preparation of the copolyester-carbonates of the instant invention generally conform to the general formula

$$R^8 \!-\! (R^9)_q \!-\! COOH \qquad XI.$$

wherein $R^9$ is an alkylene, alkylidene, aralkylene, aralkylidene or cycloaliphatic group; an alkylene, alkylidene or cycloaliphatic group containing ethylenic unsaturation; an aromatic group such as phenylene, biphenylene, substituted phenylene, and the like; two or more aromatic groups connected through non-aromatic linkages such as alkylene or alkylidene groups; and the like. $R^8$ is either a carboxyl or a hydroxyl group. The letter q represents one where $R^8$ is a hydroxyl group and either zero or one where $R^8$ is a carboxyl group.

Preferred difunctional carboxylic acids are the aromatic carboxylic acids, i.e., those wherein q is one, $R^8$ is a carboxyl or a hydroxyl group, and $R^9$ is an aromatic group such as phenylene, biphenylene, naphthylene, substituted phenylene, and the like. The preferred aromatic difunctional carboxylic acids are those represented by the general formula

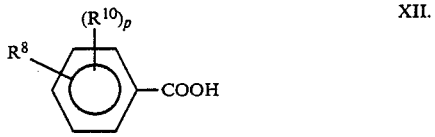

$$\qquad XII.$$

wherein $R^8$ is as defined hereinafore; p represents a whole number having a value of from 0 to 4 inclusive; and $R^{10}$ represents an inorganic atom such as chlorine, bromine, and the like; an organic group such as a monovalent hydrocarbon group, e.g., alkyl, aryl, aralkyl, alkaryl, or cycloalkyl; or an inorganic group such as the nitro group, an amine group, and the like. When more than one $R^{10}$ substituent is present they may be the same or different. $R^{10}$ is preferably a lower alkyl group.

Mixtures of two or more different difunctional carboxylic acids may be used, and where the term difunctional carboxylic acid is used herein it is meant to include mixtures of two or more different carboxylic acids as well as individual carboxylic acids.

Preferred aromatic difunctional carboxylic acids are isophthalic acid, terephthalic acid, and mixtures thereof. A particularly useful mixture of isophthalic acid and terephthalic acid is one wherein the weight ratio of isophthalic acid to terephthalic acid is in the range of from about 1:10 to about 10:1.

Rather than utilizing the difunctional carboxylic acids per se it is possible, and sometimes even preferred, to employ their reactive derivatives such as, for example, the acid halides. Particularly useful derivatives of the difunctional carboxylic acids are the acid halides. Thus, for example, instead of using terephthalic acid, isophthalic acid, or mixtures thereof it is possible to employ isophthaloyl dichloride, terephthaloyl dichloride, or mixtures thereof.

One of the methods of preparing the copolyestercarbonates of the instant invention involves the heterogeneous interfacial polymerization system utilizing an aqueous caustic solution, an organic water immiscible solvent, at least one dihydric phenol selected from dihydric phenols represented by Formulae I and II, at least one difunctional carboxylic acid or a reactive derivative thereof, a catalyst, a molecular weight regulator, and a carbonate precursor. A preferred heterogeneous interfacial polymerization system is one which utilizes phosgene as the carbonate precursor and methylene chloride or chlorobenzene as the organic solvent.

The reaction conditions, catalysts, and chain terminators or molecular weight regulators utilized are generally the same as those described hereinafore for the polycarbonates of the instant invention.

The copolyester-carbonates of the instant invention may also optionally contain admixed therewith the various additives described hereinafore.

Another embodiment of the instant invention is a copolyester-carbonate resin derived from (i) a carbonate precursor, (ii) at least one difunctional carboxylic acid or a reactive derivative thereof, (iii) at least one dihydric phenol selected from dihydric phenols represented by Formulae I and II, and (iv) at least one dihydric phenol of Formula IX. In this copolyester-carbonate the amount of the dihydric phenol of Formulae I and/or II employed is an amount effective to improve the heat resistance, e.g., glass transition temperature, of the resin. Generally this amount is from about 10 to about 90 weight %, based on the total amount of dihydric phenols present. These resins may also optionally have admixed therewith the aforedescribed additives.

Still another embodiment of the instant invention is a copolyester-carbonate resin blend comprised of (i) at least one copolyester-carbonate resin of the instant invention; and (ii) at least one copolyester-carbonate resin derived from (a) a carbonate precursor, (b) at least one difunctional carboxylic acid or a reactive derivative thereof, and (c) at least one dihydric phenol of Formula IX. These blends contain an amount of a copolyester-carbonate resin of the instant invention effective to improve the heat resistance of said blends. Generally this amount is from about 10 to about 90 weight %, based on the total amount of copolyester-carbonate resins present in the blend.

These blends may optionally contain admixed therewith the various additives described hereinafore. The instant blends may be prepared by first preforming the various resins and thereafter thoroughly mixing or blending these resins together to form an intimate physical mixture thereof.

Also included within the scope of the instant invention are the randomly branched high molecular weight thermoplastic polycarbonates and copolyestercarbonates. The randomly branched polycarbonates may be prepared by coreacting (i) a carbonate precursor, (ii) at least one dihydric phenol selected from phenols represented by Formulae I and II, and (iii) a branching agent. The copolyester-carbonates may be prepared by coreacting (i) a carbonate precursor, (ii) at least one difunctional carboxylic acid or a reactive derivative thereof (iii) at laest one dihydric phenol selected from phenols represented by Formulae I and II, and (iv) a branching agent. The branching agent is employed in minor amounts and is generally a polyfunctional organic compound generally organic in nature and containing at least three functional groups. These functional groups include carboxyl, hydroxyl, carboxylic anhydride, haloformyl, and the like. Some typical polyfunctional compounds are disclosed in U.S. Pat. Nos. 3,635,895 and 4,001,184. Some illustrative examples of these polyfunctional compounds include trimellitic anhydride, trimellitic acid, trimellityl chloride, mellitic acid, and the like.

DESCRIPTION OF THE PREFERRED EMBODIMENT

In order to more fully and clearly illustrate the present invention the following examples are set forth. It is intended that the examples be considered as illustrative rather than limiting the invention as disclosed and claimed herein. In the examples all parts and percents are on a weight basis unless otherwise indicated.

The following examples illustrate the preparation of the novel dihydric phenols of the instant invention.

EXAMPLE 1

This example illustrates the preparation of 4,4'-(cyclohexylmethylene)bisphenol (a dihydric phenol represented by Formula II).

Into a warm solution of 658.7 grams (7 moles) of molten phenol and 78.9 grams (0.7 mole) of cyclohexanecarboxaldehyde (hexahydrobenzaldehyde), placed into a 2 liter three-neck flask equipped with a stirrer, thermometer, reflux condenser and a gas-inlet tube reaching below the surface of the liquid, was introduced hydrogen chloride gas, while care was taken with the aid of a cold water cooling bath to maintain the temperature of the reaction mixture, which acquired a reddish orange color, between 34° and 45° C. After the solution became saturated with hydrogen chloride it was allowed to stand overnight at ambient temperatures, during which period white solids formed which were filtered off by suction and triturated with methylene chloride and filtered again. The resultant white crystals, which melted between 216° and 218° C., were recrystallized from methanol-water, after which they exhibited a melting point of 221°-222° C. and an assay of 99.9% by gas chromatography. $^1$H and $^{13}$C nmr confirmed the structure of the 4,4'-(cyclohexylmethylene)bisphenol. The gas chromatography retention time (GC retention/ref. in minutes) was 24.3/16.6

EXAMPLES 2-12

Following substantially the procedure outlined in Example 1 and utilizing varying amounts of corresponding phenol and aldehyde reactants various different novel dihydric phenols of the instant invention were prepared. The various dihydric phenols prepared, their melting points, their gas chromatography retention times, and their purity are set forth in Table I. Also set forth in Table I are the various corresponding phenols and aldehydes that were utilized in preparing the various dihydric phenols, as well as the amounts of these phenols and aldehydes used.

TABLE I

| Example No. | Phenol | Amount of Phenol | Aldehyde | Amount of Aldehyde | Purity % | m.p. °C. | GC retention/ref. min. | Dihydric Phenol |
|---|---|---|---|---|---|---|---|---|
| 2 | o-cresol | 325.5 gms. | cyclohexane-carboxaldehyde | 33.6 gms. | 99.7 | 121.0–122.0 | 24.7/16.4 | 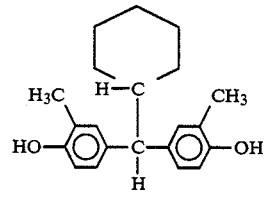 |
| 3 | 2,6-xylenol | 244 gms. | cyclohexane-carboxaldehyde | 22.4 gms. | 99.4 | 176.0–177.5 | 26.2/16.7 | 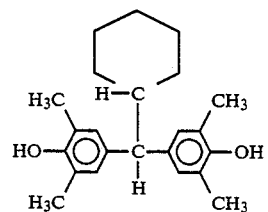 |
| 4 | phenol | 188 gms. | trimethylacet-aldehyde | 17.2 gms. | 100 | 155.0–156.0 | 21.3/16.5 | 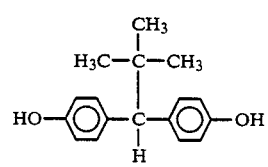 |

TABLE I-continued

| Example No. | Phenol | Amount of Phenol | Aldehyde | Amount of Aldehyde | Purity % | m.p. °C. | GC retention/ref. min. | Dihydric Phenol |
|---|---|---|---|---|---|---|---|---|
| 5 | o-cresol | 108.1 gms. | trimethylacet-aldehyde | 8.6 gms. | 98.5 | 141.0–142.0 | 21.9/16.5 | 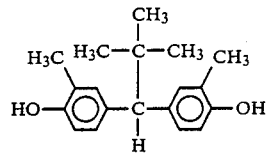 |
| 6 | 2,6-xylenol | 122 gms. | trimethylacet-aldehyde | 8.6 gms. | 99.8 | 167.5–168.5 | 23.5/166.6 | 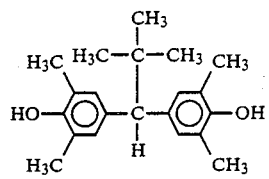 |
| 7 | phenol | 94 gms. | 2,3-dimethylbut-yraldehyde | 11.8 gms. | 98.7 | 165.5–167.0 | 21.95/16.17 | 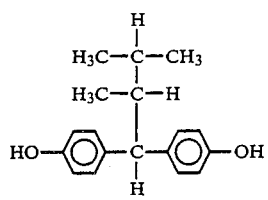 |
| 8 | 2,6-xylenol | 122 gms. | 2,3-dimethylbutyr-aldehyde | 11.8 gms | 100 | 153.0–154.4 | 23.85/16.2 | 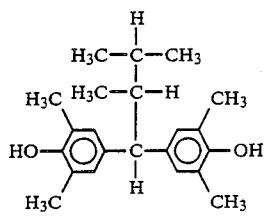 |
| 9 | phenol | 1,129.2 gms. | 2-ethylbutyr-aldehyde | 120.1 gms. | 99 | 171.0–172.0 | 20.03/14.34 | 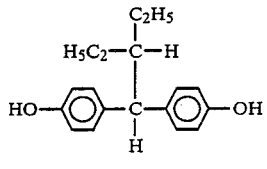 |
| 10 | 2,6-xylenol | 122 gms. | 2-ethylisovaler-aldehyde | 5.7 gms. | 100 | 162.5–164.0 | 21.84/14.12 | 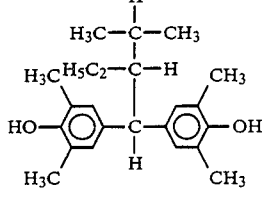 |
| 11 | 2,6-xylenol | 244.3 gms. | 2,3-dimethylvaler-aldehyde | 34.3 gms. | 99.5 | 156.0–158.0 | 24.4/16.3 | 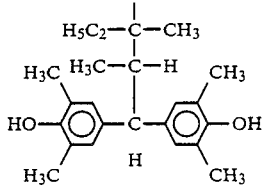 |

TABLE I-continued

| Example No. | Phenol | Amount of Phenol | Aldehyde | Amount of Aldehyde | Purity % | m.p. °C. | GC retention/ref. min. | Dihydric Phenol |
|---|---|---|---|---|---|---|---|---|
| 12 | 2,6-xylenol | 244.3 gms. | 2-phenylpropion-aldehyde | 40.3 gms. | 99.0 | 177.5–179.0 | 26.81/16.39 | 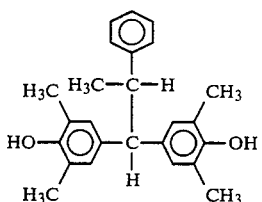 |

The following examples illustrate the preparation of the polycarbonates of the instant invention.

EXAMPLE 13

Into a mixture of 14.1 grams (0.05 mole) of 4,4'-(cyclohexymethylene)bisphenol, 300 ml of water, 400 ml of methylene chloride, 0.12 gram of phenol, and 0.28 ml of triethylamine was introduced phosgene at the rate of 0.5 gram/minute for 10 minutes while maintaining the pH of the two phase system at 11; i.e., pH 10–12.5, by the simultaneous addition of a 25% aqueous sodium hydroxide solution. At the end of the phosgenation the pH of the aqueous phase was about 11.7.

The methylene chloride phase was separated from the aqueous phase, washed with an excess of dilute (0.01N) aqueous HCl and then washed three times with deionized water. The polymer was then precipitated by steam and dried at 95° C. The resultant polycarbonate had an I.V. (intrinsic viscosity determined in methylene chloride at 25° C.) of 0.368 and a second order glass transition temperature (Tg) of 197.8° C.

EXAMPLE 14

Substantially repeating the procedure of Example 13 with a mixture of 14.1 grams (0.05 mole) of 4,4'-(cyclohexylmethylene)bisphenol and 11.4 grams (0.05 mole) of bisphenol-A, using 0.12 gram (1.25 mole %) of phenol and 0.28 ml (1.0 mole%) of triethylamine, yielded a polycarbonate of an I.V. of 0.697 dl/gm and a Tg of 183.3° C.

EXAMPLE 15

Substantially repeating the procedure of Example 14 except that a mixture of 19.77 grams (0.07 mole) of 4,4'-(cyclohexylmethylene)bisphenol and 6.85 grams (0.03 mole) of bisphenol-A was utilized, resulted in a polycarbonate having an I.V. of 0.670 dl/gm and a Tg of 190.1° C.

EXAMPLE 16

Substantially repeating the procedure of Example 14 except that a mixture of 8.5 grams (0.03 mole) of 4,4'-(cyclohexylmethylene)bisphenol and 16.0 grams (0.07 mole) of bisphenol-A was utilized, resulted in a polycarbonate having an I.V. of 0.733 dl/gm and a Tg of 172.4° C.

EXAMPLE 17

Substantially repeating the procedure of Example 13 except that a mixture of 14.1 grams (0.05 mole) of 4,4'-(cyclohexylmethylene)bisphenol and 5.75 grams (0.0125 mole) of 4,4'-(cyclohexylmethylene)bis(2,6-dimethylphenol) was utilized, resulted in a polycarbonate which had a Tg of 189.7° C.

EXAMPLE 18

Substantially repeating the procedure of Example 13 except that 31.0 grams (0.1 mole) of 4,4'-(cyclohexylmethylene)bis(2-methyphenol), 0.25 gram (2.5 mole %) of phenol and 0.28 ml (2.0 mole %) of triethylamine in 400 ml of methylene chloride and 300 ml of water were utilized, resulted in a polycarbonate having an I.V. of 0.374 dl/gm and a Tg of 170.1° C.

EXAMPLE 19

Substantially repeating the procedure of Example 13 except that 13.4 grams (0.05 mole) of 4,4'-(2,2-dimethylpropylidene)bisphenol, 0.1 gram of phenol, and 0.2 gram of triethylamine were utilized, resulted in a polycarbonate having an intrinsic viscosity of 0.544 dl/gm and a Tg of 200.4° C.

EXAMPLE 20

Substantially repeating the procedure of Example 13 except that 14.2 grams (0.05 mole) of 4,4'-(2,2-dimethylpropylidene)bis(2-methylphenol), 0.1 gram of phenol and 0.14 ml of triethylamine were utilized, resulted in a polycarbonate having an I.V. of 0.353 dl/gm and a Tg of 162.2° C.

For comparative purposes only the second order glass transition temperatures of various conventional prior art polycarbonates derived from corresponding conventional prior art dihydric phenols are presented in Table II. The polycarbonates, and the dihydric phenols from which they are derived, set forth in Table II fall outside the scope of the instant invention. In Table II the dihydric phenol from which the polycarbonate is derived, and the Tg of this polycarbonate are set forth.

TABLE II

| Dihydric Phenol | Tg of resultant polycarbonate |
|---|---|
| 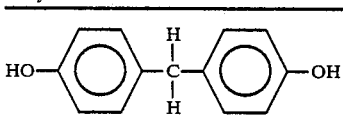 | 147° C. |
| 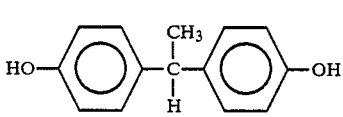 | 139° C. |

TABLE II-continued

| Dihydric Phenol | Tg of resultant polycarbonate |
|---|---|
| HO—⟨○⟩—C(C₂H₅)(H)—⟨○⟩—OH | 119.4° C. |
| HO—⟨○⟩—C(CH₃)(CH₃)—⟨○⟩—OH | 149° C. |

Comparing the Tg data in Table II with that of Examples 13–20 it is clear that the polycarbonates of the instant invention have improved glass transition temperatures over the prior art conventional polycarbonates set forth in Table II. This improvement in Tg's is quite surprising and unexpected.

As shown by the data in Table II there is no discernable pattern or correlation between the structure of the dihydric phenol and the Tg of the corresponding polycarbonate. Instead, an empirical approach must be undertaken to determine which dihydric phenols produce polycarbonates with high Tg's. The fact that the dihydric phenols of the instant invention result in polycarbonates having improved Tg's is, thus, unpredictable and unexpected.

The following examples illustrate the preparation of copolyester-carbonate resins of the instant invention.

EXAMPLE 21

To a reaction vessel there were added 14.1 grams (0.05 mole) of 4,4'-(cyclohexylmethylene)bisphenol, 0.12 gram (2.5 mole %) of phenol, 0.28 milliliter (2.0 mole %) of triethylamine, 400 milliliters of methylene chloride, and 300 milliliters of water. A 25% aqueous solution of sodium hydroxide was added to adjust the pH of the reaction mixture and thereafter maintain it at about 11. Isophthaloyl dichloride, 2.5 grams (0.0125 mole), dissolved in methylene chloride was added to the reaction mixture dropwise while maintaining the pH at 11 by the addition of the aqueous caustic solution. After the addition of the isophthaloyl dichloride was completed, and after the pH of the reaction mixture had stabilized at about 11, phosgene was introduced into the reaction mixture at the rate of 0.5 gram per minute for 10 minutes, while maintaining the pH at 11 by the use of the aqueous caustic solution. The methylene chloride layer was separated from the alkaline aqueous solution, washed with 0.01N aqueous hydrochloric acid solution, followed by two washings with deionized water. The copolyester-carbonate resin was precipitated with methanol and dried in a vacuum oven at 60° C.

The resultant copolyester-carbonate resin had an I.V. of 0.408 dl/gm and a Tg of 201.1° C.

EXAMPLE 22

The procedure of Example 21 was substantially repeated except that 5.1 grams of isophthaloyl dichloride instead of the 2.5 grams of Example 21 were employed.

The resultant copolyester-carbonate resin had a Tg of 208.1° C.

EXAMPLE 23

To a reaction veseel there were added 8.5 grams (0.03 mole) of 4,4'-(cyclohexylmethylene)bisphenol, 16.0 grams (0.07 mole) of bisphenol-A, 0.12 gram (2.5 mole %) of phenol, 0.28 milliliter (2.0 mole %) of triethylamine, 400 milliliters of methylene chloride, and 300 milliliters of water. A 25% aqueous solution of sodium hydroxide was added to adjust the pH of the reaction mixture and thereafter maintain it at about 11. Isophthaloyl dichloride, 5.1 grams (0.025 mole), dissolved in methylene chloride was added dropwise to the reaction mixture while maintaining the pH at 11 by the addition of the aqueous sodium hydroxide solution. After the addition of the isophthaloyl dichloride was completed, and after the pH of the reaction mixture has stabilized at about 11, phosgene was introduced at the rate of 0.5 grams per minute for about 16 minutes into the reaction mixture, while maintaining the pH at 11 by the use of the aqueous caustic solution. The methylene chloride layer was separated from the alkaline aqueous solution, washed with 0.01N aqueous hydrochloric acid solution, followed by two washings with deionized water. The copolyester-carbonate resin was precipitated with methanol and dried in a vacuum oven at 60° C.

The resultant copolyester-carbonate resin had an I.V. of 0.599 dl/gm and a Tg of 179.4° C.

It will thus be seen that the objects set forth above, among those made apparent from the preceding description are efficiently attained, and since certain changes may be made in carrying out the above processes and the compositions set forth without departing from the scope of the invention, it is intended that all matters contained herein sahll be interpreted as illustrative and not in a limiting sense.

What is claimed is:

1. Thermoplastic polymeric compositions exhibiting improved heat resistance comprised of (i) at least one thermoplastic polymer containing the reaction products of:
   (a) a carbonate precursor; and
   (b) at least one dihydric phenol selected from dihydric phenols represented by the general formula

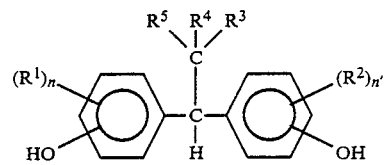

wherein
   each $R^1$ is independently selected from halogen radicals, monovalent hydrocarbon radicals, and monovalent hydrocarbonoxy radicals,
   each $R^2$ is independently selected from halogen radicals, monovalent hydrocarbon radicals, and monovalent hydrocarbonoxy radicals,
   $R^3$, $R^4$ and $R^5$ are independently selected from monovalent hydrocarbon radicals, and
   n and n' are independently selected from whole numbers having a value of from 0 to 4 inclusive.

2. The compositions of claim 1 wherein said monovalent hydrocarbon radicals represented by $R^1$ and $R^2$ are selected from alkyl radicals, aryl radicals, aralkyl radicals, alkaryl radicals, and cycloalkyl radicals.

3. The compositions of claim 1 wherein said halogen radicals represented by $R^1$ and $R^2$ are selected from chlorine and bromine.

4. The compositions of claim 1 wherein said monovalent hydrocarbonoxy radicals represented by $R^1$ and $R^2$ are selected from alkoxy radicals and aryloxy radicals.

5. The compositions of claim 1 wherein said monovalent hydrocarbon radicals represented by $R^3$, $R^4$ and $R^5$ are selected from alkyl radicals, aryl radicals, alkaryl radicals, aralkyl radicals, and cycloalkyl radicals.

6. The compositions of claim 5 wherein said monovalent hydrocarbon radicals are selected from alkyl radicals.

7. The composition of claim 5 wherein said alkyl radicals contain from 1 to about 8 carbon atoms, wherein said aryl radicals contain from 6 to 12 carbon atoms, wherein said aralkyl and alkaryl radicals contain from 7 to about 14 carbon atoms, and said cycloalkyl radicals contain from 4 to about 8 ring carbon atoms.

8. The compositions of claim 5 wherein said dihydric phenols are the 4,4'-dihydric phenols.

9. The compositions of claim 8 wherein said carbonate precursor is phosgene.

10. The compositions of claim 17 wherein $R^3$, $R^4$ and $R^5$ are independently selected from alkyl radicals.

11. The compositions of claim 10 wherein said alkyl radicals are methyl radicals.

12. The compositions of claim 11 wherein n and n' are zero.

13. The compositions of claim 1 wherein said thermoplastic polymer (i) contains the reaction products of (a); (b); and;
(c) at least one dihydric phenol represented by the general formula

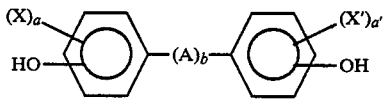

wherein:
A is selected from straight chain alkylene radicals containing from 2 to about 6 carbon atoms, straight chain alkylidene radicals containing from 2 to about 6 carbon atoms, cycloalkylene radicals containing from 4 to about 7 ring carbon atoms, cycloalkylidene radicals containing from 4 to about 7 ring carbon atoms, —S—,

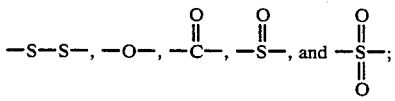

each X is independently selected from halogen radicals, monovalent hydrocarbon radicals, and monovalent hydrocarbonoxy radicals;
each X' is independently selected from halogen radicals, monovalent hydrocarbon radicals, and monovalent hydrocarbonoxy radicals;
b is either zero or one; and
a and a' are independently selected from whole numbers having a value of from 0 to 4 inclusive.

14. The compositions of claim 13 which contain an amount of dihydric phenol of (b) effective to improve the heat resistance of said compositions.

15. The compositions of claim 14 wherein said amount is in the range of from about 10 to about 90 weight percent, based on the total amount of dihydric phenols present.

16. The compositions of claim 15 wherein said dihydric phenols (c) are the 4,4'-bisphenols.

17. The compositions of claim 16 wherein said 4,4'-bisphenol is bislphenol-A.

18. The compositions of claim 1 which further contain (ii) at least one thermoplastic polycarbonate resin containing the reaction products of:
(d) a carbonate precursor; and
(e) at least on dihydric phenol represented by the general formula

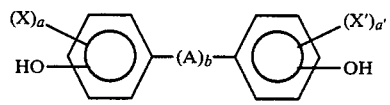

wherein:
A is selected from straight chain alkylene radicals containing from 2 to about 6 carbon atoms, straight chain alkylidene radicals containing from 1 to about 6 carbon atoms, cycloalkylene radicals containing from 4 to about 7 ring carbon atoms, cycloalkylidene radicals containing from 4 to about 7 ring carbon atoms,

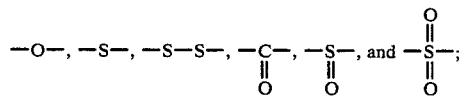

each X is independently selected from halogen radicals, monovalent hydrocarbon radicals, and monovalent hydrocarbonoxy radicals;
each X' is independently selected from halogen radicals, monovalent hydrocarbon radicals, and monovalent hydrocarbonoxy radicals;
b is either zero or one; and
a and a' are independently selected from whole numbers having a value of from 0 to 4 inclusive.

19. The compositions of claim 18 which contain an amount of polymer of (i) effective to improve the heat resistance of said compositions.

20. The compositions of claim 19 wherein said amount is in the range of from about 10 to about 90 weight percent, based on the total amount of polymers (i) and (ii) present.

21. The compositions of claim 20 wherein b is one and A is selected from alkylene radicals, alkylidene radicals, cycloalkylene radicals, and cycloalkylidene radicals.

22. The compositions of claim 21 wherein said dihdric phenol of (ii) (e) is a 4,4'-bisphenol.

23. The compositions of claim 22 wherein said bisphenol is bisphenol-A.

24. The compositions of claim 1 wherein said polymer (i) contains the reaction products of (a); (b); and
(f) at least one difunctional carboxylic acid or a reactive derivative thereof.

25. The compositions of claim 24 wherein said reactive derivative of said difunctional carboxylic acid is an acid dihalide.

26. The compositions of claim 25 wherein said acid dihalide is an acid dichloride.

27. The compositions of claim 26 wherein said acid dichlorides are selected from isophthaloyl dichloride, terephthaloyl dichloride, and mixtures thereof.

28. The compositions of claim 24 wherein said monofunctional hydrocarbon radicals represented by $R^3$, $R^4$ and $R^5$ are selected from alkyl radicals, aryl radicals, alkaryl radicals, aralkyl radicals, and cycloalkyl radicals.

29. The compositions of claim 28 wherein said dihydric phenol is a 4,4'-bisphenol.

30. The composition of claim 24 wherein said polymer (i) contains the reaction products of (a); (b); (f); and (g) at least one dihydric phenol represented by the general formula

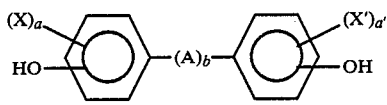

wherein:

A is selected from straight chain alkylene radicals containing from 2 to about 6 carbon atoms, straight chain alkylidene radicals containing from 1 to about 6 carbon atoms, cycloalkylene radicals containing from 4 to about 7 ring carbon atoms, cycloalkylidene radicals containing from 4 to about 7 ring carbon atoms,

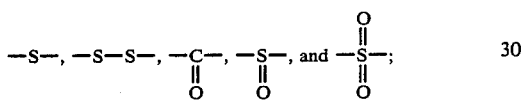

each X is independently selected from halogen radicals, monovalent hydrocarbon radicals, and monovalent hydrocarbonoxy radicals;

each X' is independently selected from halogen radicals, monovalent hydrocarbon radicals, and monovalent hydrocarbonoxy radicals;

b is either zero or one; and a and a' are independently selected from whole numbers having a value of from 0 to 4, inclusive.

31. The compositions of claim 30 which contain an amount of said dihydric phenol (b) effective to improve the heat resistance thereof.

32. The compositions of claim 31 wherein said amount is in the range of from about 10 to about 90 weight percent, based on the total amount of dihydric phenols employed.

33. The compositions of claim 32 wherein said monovalent hydrocarbon radicals represented by X and X' are selected from alkyl radicals, aryl radicals, aralkyl radicals, alkaryl radicals, and cycloalkyl radicals.

34. The compositions of claim 33 wherein A is selected from alkylene radicals, alkylidene radicals, cycloalkylene radicals, and cycloalkylidene radicals.

35. The compositions of claim 34 wherein said dihydric phenols are 4,4'-bisphenols.

36. The compositions of claim 35 wherein said 4,4'-bisphenol is bisphenol-A.

37. The compositions of claim 24 which further contain (iii) at least one polymer containing the reaction products of
(g) a carbonate precursor;
(h) at least one difunctional carboxylic acid or a reactive derivative thereof; and
(i) at least one dihydric phenol represented by the general formula

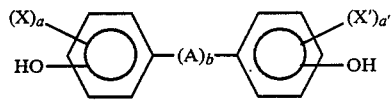

wherein:

A is selected from straight chain alkylene radicals containing from 2 to about 6 carbon atoms, straight chain alkylidene radicals containing from 1 to about 6 carbon atoms, cycloalkylene radicals conatining from 4 to about 7 ring carbon atoms, cycloalkylidene radicals containing from 4 to about 7 ring carbon atoms,

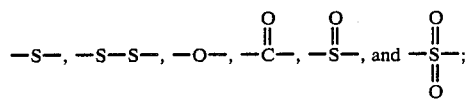

each X is independently selected from halogen radicals, monovalent hydrocarbon radicals, and monovalent hydrocarbonoxy radicals;

each X' is independently selected from halogen radicals, monovalent hydrocarbonoxy radicals, and monovalent hydrocarbon radicals;

b is either one or zero; and a and a' are independently selected from whole numbers having a value of from 0 to 4 inclusive.

38. The compositions of claim 37 which contain an amount of polymer (i) effective to improve the heat resistance of said compositions.

39. The compositions of claim 38 wherein said amount is from about 10 to about 90 weight percent, based on the amount of polymers (i) and (iii) present.

40. The compositions of claim 39 wherein said dihydric phenol (i) is bisphenol-A.

* * * * *

UNITED STATES PATENT AND TRADEMARK OFFICE
CERTIFICATE OF CORRECTION

PATENT NO. : 4,520,187
DATED : May 28, 1985
INVENTOR(S) : Victor Mark and Charles V. Hedges It is certified that error appears in the above-identified patent and that said Letters Patent is hereby corrected as shown below:

Column 21, line 24 - claim 10 remove "claim 17" and add "claim 9".

Signed and Sealed this

Twenty-third Day of February, 1988

Attest:

DONALD J. QUIGG

*Attesting Officer*     *Commissioner of Patents and Trademarks*